United States Patent
Barth et al.

(10) Patent No.: US 6,586,601 B1
(45) Date of Patent: Jul. 1, 2003

(54) METHOD FOR PRODUCING 2-HALOPYRIDINE-N-OXIDE

(75) Inventors: Volker Barth, Ludwigshafen (DE); Bruno Biedenbach, Worms (DE); Karl Hermes, Bensheim (DE); Stefan Sendelbach, Neckarsulm (DE); Dieter Weinzierl, Bobenheim (DE)

(73) Assignee: Ruetgers Organics GmbH, Mannheim (DE)

( * ) Notice: Subject to any disclaimer, the term of this patent is extended or adjusted under 35 U.S.C. 154(b) by 0 days.

(21) Appl. No.: 09/720,378

(22) PCT Filed: Jul. 21, 1999

(86) PCT No.: PCT/EP99/05184

§ 371 (c)(1),
(2), (4) Date: Dec. 26, 2000

(87) PCT Pub. No.: WO00/06548

PCT Pub. Date: Feb. 10, 2000

(30) Foreign Application Priority Data

Jul. 30, 1998 (DE) .......................................... 198 34 336

(51) Int. Cl.[7] ............................................. C07D 213/61

(52) U.S. Cl. ......................... 546/345; 546/345; 549/297

(58) Field of Search ........................... 546/345; 549/297

(56) References Cited

PUBLICATIONS

Saika et al, Chem. Abstract vol. 111 No. 38657, Indian J. Chem. Sect. A, vol. 27A(9) pp. 790–793, 1988.*

\* cited by examiner

*Primary Examiner*—Alan L. Rotman
*Assistant Examiner*—Raymond Covington
(74) *Attorney, Agent, or Firm*—Foley & Lardner

(57) ABSTRACT

The present invention concerns a process for the preparation of 2-halopyridine N-oxide by reaction of 2-halopyridine with hydrogen peroxide in aqueous solution in the presence of an acid anhydride as catalyst in which, according to the invention, as catalyst there is used an anhydride of the formula I

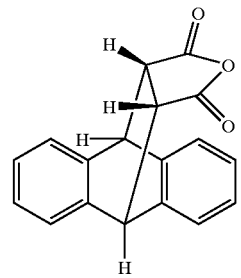

whereby the aromatic rings can be substituted by alkyl groups or halogens or can be anellated with a further aromatic ring.

18 Claims, No Drawings

METHOD FOR PRODUCING 2-HALOPYRIDINE-N-OXIDE

This application is a 371 of PCT/EP99/05184 filed Jul. 21, 1999.

The subject of the present invention is an improved process for the preparation of 2-halopyridine N-oxide.

2-Halopyridine N-oxides, especially 2-chloropyridine N-oxide, are important intermediate products for example in the preparation of pyrithiene, especially zinc pyrithione, which are effective as bactericides and fungicides.

Because of the electron-attracting properties of the halogens, 2-halopyridines can be oxidised with greater difficulty than other pyridine derivatives.

Therefore, there was first described the carrying out of the oxidation with peroxy acids whereby, however, the reaction is only incomplete and a multiple recycling of the unreacted starting material is necessary. Furthermore, such peroxy acids are comparatively expensive and unstable (U.S. Pat. No. 2,951,844).

From U.S. Pat. No. 4,504,667, it is further known that 2-halopyridines can be reacted by means of peracetic acid with higher yields to give 2-halopyridine N-oxides when the peracetic acid is formed in situ from acetic acid and $H_2O_2$ in the presence of a catalyst. As catalyst, there are used maleic acid, maleic acid anhydride or phthalic acid anhydride in an amount of 0.1–0.8 mol/mol pyridine. A disadvantage of this process is that unreacted halopyridine must be laboriously removed, after neutralisation of the solution, by steam distillation and the added acetic acid and the catalyst remain in the aqueous phase as salts and thus are lost.

An improvement is described in U.S. Pat. No. 3,047,579, whereby 2-chloropyridine is reacted with hydrogen peroxide in the presence of pertungstic acid as catalyst. Here, too, the reaction with about 68%, with use of an excess of $H_2O_2$, is only incomplete, therefore requires a laborious working up and purification and especially a working up again of the expensive environmentally damaging heavy metal catalysts.

The U.S. Pat. No. 3,203,957 shows a further important advance, according to which the oxidation of 2-chloropyridine in an organic solvent is carried out with addition of aqueous 70% hydrogen peroxide and maleic acid anhydride. Conversions of over 50% are thereby achieved. A disadvantage of this process is that the maleic acid anhydride must be used in at least equimolar amount referred to the chloropyridine and thus large amounts of maleic acid are formed as waste products of the reaction which must be washed out from the reaction mixture with caustic soda solution and either disposed of as waste or can again be laboriously converted back into maleic acid anhydride. The separating off of the unreacted halopyridine after this process also makes difficulties.

Therefore, the task exists to find an improved process for the preparation of 2-halopyridine N-oxide, especially of 2-chloropyridine N-oxide, which can be carried out simply and economically.

The solution of this task is made possible by the features of the main claim and promoted by the features of the subsidiary claims.

Maleic acid anhydride and anthracene can be condensed (cf. O. Diels, K. Alder, "Annalen der Chemie, 486, pp. 191–202 (1931) and E. Clar, Annalen der Chemie, 486, 2194–2200 (1931)) in a Diels-Alder reaction to give a polycyclic compound (9,10-dihydro-9,10-ethane-anthracene-11,12-dicarboxylic acid anhydride) of the following formula I

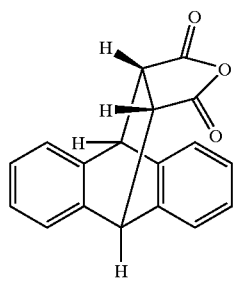

formula I

This condensation product reacts with $H_2O_2$ to give the peroxy acid of the formula II,

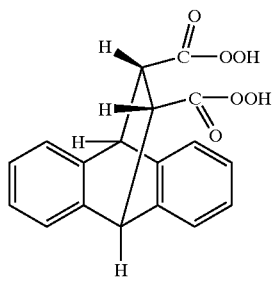

formula II which is able to oxidise 2-halopyridine to the N-oxide. Surprisingly, the acid thereby formed of the formula III

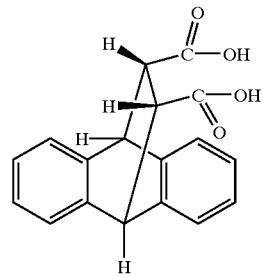

formula III under the reaction conditions, in spite of the water present in excess, is returned into the anhydride so that catalytic amounts of this compound suffice in order to make possible a complete reaction with the $H_2O_2$.

In contradistinction thereto, the reactions described in U.S. Pat. No. 3,203,957 require an at least equimolar amount of maleic acid anhydride or phthalic acid anhydride since, in the case of the reaction, the no longer catalytically acting maleic acid or phthalic acid is formed. In the case of the working up of the reaction batch, the small amounts of the catalyst of formula I remain preponderantly in the unreacted 2-halopyridine and can thus always again be returned into the reaction. A laborious purification and recovery of the catalyst is thereby unnecessary.

It is assumed that, instead of anthracene, other anthracene derivatives can also be used, such as the higher polycyclenes naphthacene or benz(a)anthracene, as well as the anthracenes substituted in the outer ring systems by alkyl or halogen which, in the same way, are still capable of a Diels-Alder reaction with maleic acid anhydride. These condensation products are, in the following, also to be regarded as being included by the designation anhydride I. It appears to be decisive that the reformation of the anhydride I from the acid is favoured via the steric fixing of the neighbouring carbon, whereby a use of merely catalytic amounts of this compound is possible and, on the other hand, the large aromatic radical brings about the solubility of this compound in the organic phase so that the catalyst compound remains behind in the case of the purification of 2-chloropyridine N-oxide. Less hindered Diels-Alder products, for example the cyclohexene-4,5-dicarboxylic acid anhydride formed from butadiene and MA or the cis-5-norbornene-endo-2,3-dicarboxylic acid anhydride formed with cyclopentadiene, appear not to be capable for the intermediate reformation of the anhydride since the reaction with hydrogen peroxide breaks off after consumption of the catalyst.

A preferred process variant consists in mixing 2-chloropyridine with catalytic amounts of the anhydride I, for example 1 to 25%, preferably 10 to 15%, and to add to this mixture, at temperatures between 50 and 100° C., preferably about 70 to 80° C., aqueous hydrogen peroxide with stirring. As hydrogen peroxide, there is used a commercially available 50 to 70% solution. After complete addition of the hydrogen peroxide, e.g. in a time of 0.5 h, in general it is kept further for about 1 to 3 h at the reaction temperature, thereafter cooled and the reaction phase extracted with water. The aqueous phase is worked up in per se known manner to 2-halopyridine N-oxide. The organic phase which, besides the unreacted halopyridine, contains small amounts of halopyridine N-oxide and the catalyst, is recycled into the next batch so that in this regard no losses occur. After the addition of fresh 2-halopyridine, this phase can be directly used again for subsequent reactions without further purification.

The reaction normally takes place without addition of solvents since the 2-chloropyridine sufficiently fulfils this purpose but an addition of an inert solvent is possible, for example of a chlorohydrocarbon, such as methylene chloride, of a paraffin hydrocarbon, such as cyclohexane or N-heptane, in order to dilute the reaction batch and, in the subsequent extraction with water, to promote the phase separation.

Since the catalyst is not hydrolysed with water, it is possible that the reaction mixture initially already contains water, for example from the preceding reaction cycle, whereby about 3–5% of water remain in the organic phase, or by direct addition of 3–20% of water. Otherwise, the water which is introduced with the hydrogen peroxide is dissolved in the warm reaction solution without formation of a second phase. An aqueous phase is first formed in the cold by addition of water, for example 25–100% of the mixture. Larger amounts are not useful since the working up costs increase, smaller amounts lead to a slower phase separation. Since the halopyridine N-oxide formed can be separated from unreacted halopyridine by extraction with water, in the sense of an economic reaction it is advantageous to work with an insufficiency of hydrogen peroxide. Hydrogen peroxide in an amount of 0.5 to one equivalent are thereby preferred. Since, as is known, in the case of the reaction, about 50% of the peroxide used is removed from the reaction via a breakdown into $H_2O$ and $O_2$, only 20–50% of the chloropyridine used are reacted, the remainder remains behind as solvent for the catalyst (organic phase). On the other hand, the reaction can naturally also be controlled by addition of $H_2O_2$ in excess having regard to a substantially quantitative reaction. Depending thereon, high yields are obtained having regard to the peroxide used or to the pyridine derivative used.

EXAMPLE 1

Example of Use: Preparation Procedure for 2-Chloropyridine N-oxide:

a) Start of the Reaction

To 454 g 2-chloropyridine, one adds 65 g anhydride 1 and heats to 80° C. Within 2 hours, one adds dropwise thereto 140 g 70% hydrogen peroxide. Subsequently, one allows to after-react for 3 hours at this temperature. Thereafter, one cools and extracts three times with, in each case, 180 g of water. The aqueous phases are combined and pass to the preparation of 2-mercaptopyridine N-oxide. The yield amounts to 150 g 2-chloropyridine N-oxide. The organic phase (304 g chloropyridine, 5 g chloropyridine N-oxide, 20 g $H_2O$, 64 g anhydride) is used again for the next oxidation.

b) Further Oxidation of the Organic Phase

The organic phase from the above procedure is mixed with 150 g fresh 2-chloropyridine. Subsequently, one heats to 80° C. and further proceeds as described above. Yield of 2-chloropyridine N-oxide 155 g.

After 10 cycles, the total conversion referred to the anhydride 1 used (of which still about 55–58 g are contained) amounts to 4500%.

EXAMPLE 2

Example of Use: Preparation of 2-Chloropyridine N-oxide (Presence of Water at Beginning of the Reaction)

To 454 g 2-chloropyridine one adds 65 g anhydride I and 18 g water and heats to 80° C. Within 2 hours, one adds dropwise thereto 140 g 70% hydrogen peroxide. Subsequently, one allows to after-react for 3 hours at this temperature. Thereafter, one cools and extracts three times with, in each case, 180 g of water. The aqueous phases are combined and pass to the preparation of 2-mercaptopyridine N-oxide. The yield amounts to 155 g 2-chloropyridine N-oxide. The organic phase is used for the next oxidation.

EXAMPLE 3

Addition of an Organic Solvent in the Case of the Working Up a) The first preparation of 2-chloropyridine N-oxide took place according to Example 1. Before the stirring up with water, 100 g 1,2-dichloroethane were added thereto. The phase separation was ended more quickly than without dichloroethane addition. The yield amounted to 175 g 2-chloropyridine N-oxide.

b) The separated off organic phase from the above described Example was mixed with 176 g 2-chloropyridine and, in known manner, again reacted to give 2-chloropyridine N-oxide. The 1,2-dichloroethane contained in the organic phase did not change the reaction in comparison with Example 1b). The phase separation in the case of stirring up with water again took place somewhat more quickly than previously. The yield amounted to 174 g 2-chloropyridine N-oxide.

EXAMPLE 4

Working Up of the Aqueous Extracts

The aqueous extracts are normally further worked up directly. For the obtaining of the pure product, the aqueous phase is extracted with chloroform, whereby a previous alkalisation improves the transfer into the organic phase. By distilling off of the solvent and drying of the remaining 2-chloropyridine N-oxide in a vacuum, the pure solid material is obtained.

EXAMPLE 5 (Comparison)

Use of Alternative Catalysts a) Use of cis-5-Norbornene-endo-2,3-dicarboxylic Acid Anhydride (Diels-Alder Adduct From Cyclopentadiene and Maleic Acid Anhydride)

24 g (0.15 mol) catalyst in 289 g 2-chloropyridine were reacted with 89 g hydrogen peroxide as in the above Examples of use. Yield 28.4 g of impure 2-chloropyridine N-oxide.

b) Use of cis-4-Cyclohexene-1,2-dicarboxylic Acid Anhydride (Diels-Alder Adduct of Butadiene and Maleic Acid Anhydride)

Mole ratios and batch size as before. The experiment gave large amounts of unreacted hydrogen peroxide. The yield of 2-chloropyridine N-oxide amounted to only 10 g of impure 2-chloropyridine N-oxide.

What is claimed is:

1. Process for the preparation of 2-halopyridine N-oxide by reaction of 2-halopyridine with a 50 to 70% aqueous hydrogen peroxide solution in the presence of an acid anhydride catalyst at temperatures of 50° C. to 100° C., wherein as catalyst, there is used an anhydride of the formula I

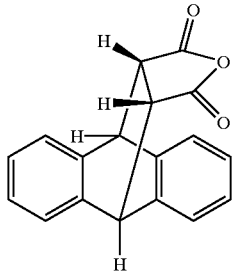

whereby the aromatic rings can be substituted by alkyl groups or halogens or can be anellated with a further aromatic ring, whereby, referred to the 2-halopyridine a) the anhydride is used in an amount of 1 to 25% and
b) the hydrogen peroxide is used in an amount of at least 0.5 equivalents.

2. Process according to claim 1, wherein in the case of the reaction, an inert solvent is additionally used.

3. Process according to claim 1, wherein the resulting 2-halopyridine N-oxide is separated from the reaction solution by extraction with water and the non-aqueous phase is used for the next reaction batch.

4. Process according to claim 1, wherein to the reaction mixture of halopyridine and catalyst, up to 20% of water is added before the addition of hydrogen peroxide.

5. Process according to claim 1, wherein $H_2O_2$ is used in an amount of up to 1 equivalent, referred to the 2-halopyridine.

6. Process according to claim 1, wherein 2-chloropyridine is used as 2-halopyridine.

7. Process according to claim 2, wherein the resulting 2-halopyridine N-oxide is separated from the reaction solution by extraction with water and the non-aqueous phase is used for the next reaction batch.

8. Process according to claim 2, wherein to the reaction mixture of halopyridine and catalyst, up to 20% of water is added before the addition of hydrogen peroxide.

9. Process according to claim 3, wherein to the reaction mixture of halopyridine and catalyst, up to 20% of water is added before the addition of hydrogen peroxide.

10. Process according to claim 2, wherein $H_2O_2$ is used in an amount of up to 1 equivalent, referred to the 2-halopyridine.

11. Process according to claim 3, wherein $H_2O_2$ is used in an amount of up to 1 equivalent, referred to the 2-halopyridine.

12. Process according to claim 4, wherein $H_2O_2$ is used in an amount of up to 1 equivalent, referred to the 2-halopyridine.

13. Process according to claim 2, wherein 2-chloropyridine is used as 2-halopyridine.

14. Process according to claim 3, wherein 2-chloropyridine is used as 2-halopyridine.

15. Process according to claim 4, wherein 2-chloropyridine is used as 2-halopyridine.

16. Process according to claim 5, wherein 2-chloropyridine is used as 2-halopyridine.

17. A process for the preparation of 2-halopyridine N-oxide comprising:

reacting, at temperatures of 50° C. to 100° C., 2-halopyridine with 50 to 70% aqueous hydrogen peroxide solution in the presence of an acid anhydride catalyst of formula I:

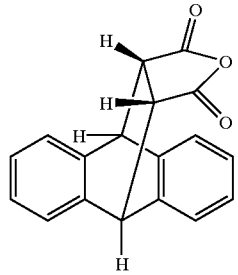

wherein aromatic rings of said catalyst of formula I may be substituted by alkyl groups or halogens or may be anellated with a further aromatic ring, wherein said catalyst is present in an amount of 1–25% with respect to said 2-halopyridine, and wherein said hydrogen peroxide is present in an amount of at least 0.5 equivalents based on 2-halopyridine.

18. Process for the preparation of 2-halopyridine N-oxide by reaction of 2-halopyridine with a 50 to 70% aqueous hydrogen peroxide solution in the presence of an acid anhydride catalyst at temperatures of 50° C. to 100° C., wherein as catalyst, there is used an anhydride of the formula I

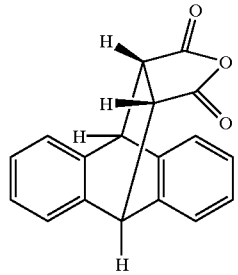

whereby, referred to the 2-halopyridine a) the anhydride is used in an amount of 1 to 25% and
b) the hydrogen peroxide is used in an amount of at least 0.5 equivalents.

* * * * *